United States Patent [19]

Holtkamp, Sr.

[11] Patent Number: Plant 7,029

[45] Date of Patent: Sep. 12, 1989

[54] AFRICAN VIOLET PLANT NAMED LITTLE PEARL

[76] Inventor: Reinhold Holtkamp, Sr., Werther Strasse 112, D4294 Isselburg, Fed. Rep. of Germany

[21] Appl. No.: 262,592

[22] Filed: Oct. 26, 1988

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Little Pearl which is a sport of Little Rose Quartz disclosed in U.S. Pat. No. 6110. Little Pearl is characterized by its miniature growth habit; very light pinkish white, semi-double flowers; 7–9 petals per flower, the ones in the center being much smaller and covering up the anthers; strong stems which curve toward the center to form a compact bouquet above the leaves; profuse and continuous flowering; medium green, spear to heart-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Pearl.

The new cultivar was referred to during the breeding and selection process by the designation M/H 540 and is a sport of Little Rose Quartz, disclosed in my U.S. Plant Pat. No. 6,110, granted Feb. 16, 1988. The female, or seed parent of Little Rose Quartz was a cultivar designated *Saintpaulia schumensis.* The male, or pollen parent of Little Rose Quartz was a cultivar designated Z41/S Mini pink. Little Pearl is similar in all essential respects to Little Rose Quartz except for its pinkish white color and the larger size of the petals. Little Pearl was discovered in a flowering block of the parent cultivar Little Rose Quartz, and subsequently selected. Asexual reproduction of the new leaf cultivar by leaf cuttings, as performed by me at Haffen, West Germany, has demonstrated that the combination of characteristics as herein disclosed for the new cultivar are firmly fixed and retained through successive generations of asexual reproduction.

Little Pearl has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Pearl, which in combination distinguish this african violet as a new and distinct cultivar:

(1) Little Pearl is a miniature and will not grow taller than 6 cm.
(2) Very light pinkish white semi-double flowers.
(3) Strong wirelike and upright flower stems curving toward the center.
(4) First flash of flowers form a tight bouquet above the leaves.
(5) Profuse flowering and continuous blooming.

(6) Each plant carries 8 and more upright flower stems each of which carries 5 and more flowers.
(7) Long lasting, non-dropping flowers.
(8) Plant saleable 10 to 11 weeks after planting of unrooted shoot.
(9) Seed capsules push slightly through.
(10) Medium green hairy leaves.
(11) Spear to heart-shaped leaves are 1.5 to 2.3 cm in length.
(11) After maturity the flowers dry off and remain on the peduncle.

The accompanyng color photographic drawing shows a typical specimen plant of the new cultivar grown in a 4 cm pot. The plant is pictured next to a pencil, highlighting the miniature size and growth habit of Little Pearl. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 1 p.m. in Nashville, Tenn.

Botanical classification: *Saintpaulia ionantha,* Ramat., c.v. Little Pearl.

Parentage: Sport of Little Rose Quartz, disclosed in U.S. Plant Pat. No. 6,110.

Propagation: The new cultivar holds its distinguishing characteristics through successive propagations by leaf cuttings.

Plant: From 5 to 6 cm tall when grown in pots, and approximately 8–10 cm in diameter when fully grown.

*Leaves.*—General form: Spear to heart-shaped. Diameter: 18–22 mm wide and 20–23 mm long. Texture: Leatherlike. Aspect: Shiny, hairy. Veins: Upperside: visible; underside: well pronounced, light green, shiny; light green between the veins. Color (upperside): Yellow-Green Group 147 A. Color (underside): Yellow-Green Group 148 D. Petiole: Strong upright, reddish green, hairy.

*Flowers.*—Buds: Size: 3–4 mm just before opening. Shape: Bell-shaped. Color: Light green. Sepals: Five (5). Color: Greenish brown. Calyx: Shape: Funnel-shaped. Aspect: Spear-shaped, hairy. Peduncle: Character: Strong, wirelike, upright hairy. Color: Brownish green. Individual flowers: Size: 20–23 mm. Shape: Semi-double, violet-shaped, (7–9 petals per flower); occasionally single. Color (upperside): Red Group 56 D and lighter. Under cooler temperatures and more intensive lighting, the pinkish touch tends to intensify. Color (underside): Red Group 56 D and lighter. Borne: Each flower stem carries 5 and more flowers on strong, upright peduncle that are free standing above the leaves, thereby forming a compact bouquet. Flowering habit: Flowers 10–11 weeks after planting an unrooted plantlet.

*Reproductive organs.*—Stamens: Two (2), mostly hidden due to flower form. Anthers: 2 composed of 4 anther cells, seed capsule pushes slightly through. Filaments: Yellowish green, 2 mm long. Styles: 3–4 mm long, white, base of ovary light green and hairy.

*Roots.*—Normally developed, white when young, turning slightly brownish when older.

Disease resistance: Good.

General observations: Little Pearl is a super miniature violet, which does not grow taller than 5–6 cm. The very light pinkish white, semi-double flowers are composed of 7–9 petals, the ones in the center being much smaller and covering up the anthers. Occasionally the flowers are single and have a pink tinge in the center. The flowers are very long-lasting and non-dropping. Little Pearl has continuous blooming characteristics, and under good growing conditions it will not stop blooming. A nice bouquet of flowers free standing above the leaves develops approximately 10–11 weeks after planting an unrooted plantlet. Each of the 8 and more strong flower stems carries 5 and more flowers. The medium green leaves are spear to heart-shaped.

I claim:

1. A new and distinct cultivar of African violet named Little Pearl, as described and illustrated, and particularly characterized by its miniature growth habit; very light pinkish white, semi-double flowers; 7–9 petals per flower, the ones in the center being much smaller and covering up the anthers; strong stems which curve toward the center to form a compact bouquet above the leaves; profuse and continuous flowering; medium green, spear to heart-shaped leaves; flowering 10–11 weeks after planting of unrooted shoot, and by its long lasting and non-dropping flowers.

* * * * *

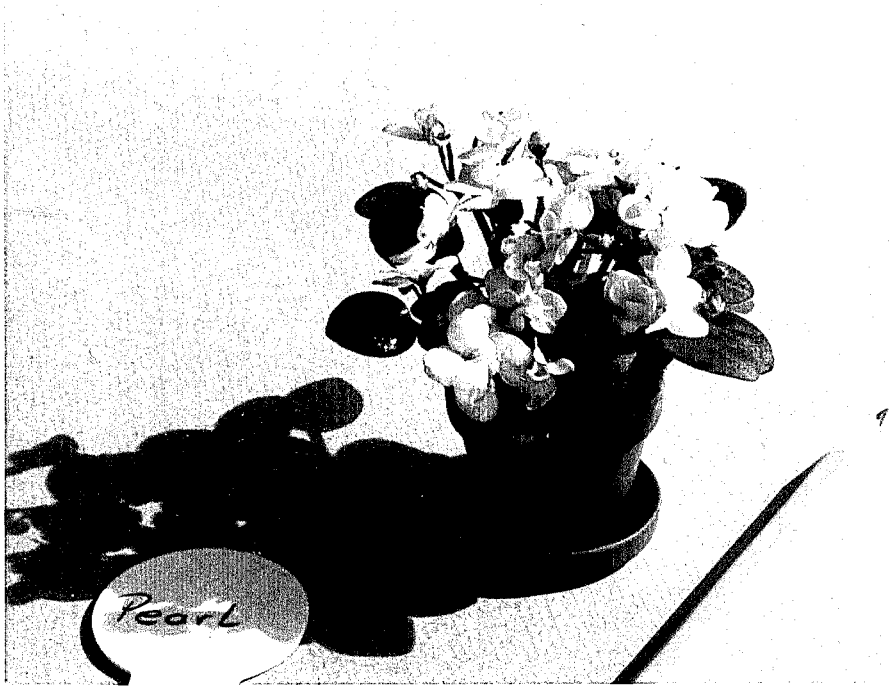
Pearl